(12) United States Patent
Reynolds (10) Patent No.: US 9,241,883 B2
(45) Date of Patent: Jan. 26, 2016

(54) IONIC COMPLEXES

(71) Applicant: The University of Melbourne, Parkville, Victoria (AU)

(72) Inventor: Eric Charles Reynolds, Carlton (AU)

(73) Assignee: The University of Melbourne, Parkville, Victoria (AU)

( * ) Notice: Subject to any disclaimer, the term of this patent is extended or adjusted under 35 U.S.C. 154(b) by 104 days.

(21) Appl. No.: 14/074,022

(22) Filed: Nov. 7, 2013

(65) Prior Publication Data

US 2014/0056824 A1    Feb. 27, 2014

Related U.S. Application Data

(63) Continuation of application No. 11/917,395, filed as application No. PCT/AU2006/000885 on Jun. 23, 2006, now Pat. No. 8,603,988.

(60) Provisional application No. 60/694,019, filed on Jun. 24, 2005.

(51) Int. Cl.
*A61K 6/00* (2006.01)
*A23L 2/39* (2006.01)
*A61K 8/24* (2006.01)
*A61K 8/64* (2006.01)
*A61Q 11/00* (2006.01)

(52) U.S. Cl.
CPC ... *A61K 8/24* (2013.01); *A61K 8/64* (2013.01); *A61Q 11/00* (2013.01); *A61K 2800/52* (2013.01)

(58) Field of Classification Search
None
See application file for complete search history.

(56) References Cited

U.S. PATENT DOCUMENTS

| | | | |
|---|---|---|---|
| 4,522,805 A | 6/1985 | Gordan | |
| 5,015,628 A | 5/1991 | Reynolds | |
| 6,056,930 A | 5/2000 | Tung | |
| 6,780,844 B1 | 8/2004 | Reynolds | |
| 7,312,193 B2 | 12/2007 | Reynolds | |
| 7,491,694 B2 | 2/2009 | Reynolds et al. | |
| 8,603,988 B2* | 12/2013 | Reynolds ................. | A61K 8/24 433/217.1 |
| 2002/0028251 A1 | 3/2002 | Okay | |
| 2005/0063922 A1 | 3/2005 | Reynolds et al. | |
| 2005/0089481 A1* | 4/2005 | Yamanaka ............... | A61K 8/24 424/50 |

FOREIGN PATENT DOCUMENTS

| | | |
|---|---|---|
| EP | 1 525 878 A1 | 4/2005 |
| JP | 10-290682 A | 11/1998 |
| JP | 11-310599 A | 11/1999 |
| JP | 3742523 | 11/1999 |
| JP | 2004-215521 A | 8/2004 |
| WO | 87/07615 A1 | 12/1987 |
| WO | 93/03707 A1 | 3/1993 |
| WO | 94/00146 A1 | 1/1994 |
| WO | 98/40406 A1 | 9/1998 |
| WO | 00/57892 A1 | 10/2000 |
| WO | 01/44106 A1 | 6/2001 |
| WO | 02/094204 A1 | 11/2002 |
| WO | 03/059303 A2 | 7/2003 |
| WO | 03/059304 A1 | 7/2003 |
| WO | 2004/035077 A1 | 4/2004 |
| WO | 2004/054531 A1 | 7/2004 |
| WO | 2006/130913 A1 | 12/2006 |

OTHER PUBLICATIONS

Adamson et al., "The Analysis of Multiple Phosphoseryl-Containing Casein Peptides Using Capillary Zone Electrophoresis", J. Chromatogr., 646(2):391-396. (Sep. 3, 1993).

Adamson et al., "Characterisation of Tryptic Casein Phosphopeptides Prepared Under Industrially-Relevant Conditions", Biotec. Bioeng, 45:196-4 (1995).

Adamson et al., "High Performance Capillary Electrophoresis of Casein Phosphopeptides Containing 2-5 Phosphoseryl Residues; Relationship Between Absolute Electrophoretic Mobility and Peptide Charge and Size", Electrophoresis 16:525-528 (1995).

Adebayo, O.A., et al., "Effects of conditioners on microshear bond strength to enamel after carbamide peroxide bleaching and/or casein phosphopeptide-amorphous calcium phosphate (CPP-ACP) treatment", Journal of Dentistry, 35:862-870 (2007).

Allais, G., "Karies—Die Therapie", Journal of Continuing Dental Education, pp. 716-735. English Abstract (Jun. 2007).

Al-Zraikat, H., et al., "Development of glass ionomer cement incorporating casein phosphopetide amorphous phosphate (CPP-ACP) complex", Australian Dental Journal ADRF Special Research Supplement, 52(4):S4 (2007).

Al-Zraikat, H. et al., "Incorporation of casein-phosphopeptide-amorphous calcium phosphate into glass ionomer cement." Abstract 0654—84th General Session of the IADR, Brisbane, Australia (Jun. 28-Jul. 1, 2006).

Angmar, B., et al., "Studies on tile Ulatrastructure of Dental Enamel." J. Ultrastructure Research, 8:12-23 (1963).

Aoba, T., et al., "Dental Fluorosis: Chemistry and Biology."Crit Rev Oral Biol Med. 13(2):155-170 (2002).

Ardu, S. et al., "A minimally invasive treatment of severe dental fluorosis", Quintessence International, 38(6):455-458 (Jun. 2007).

Ardu, S. et al., "Minimally invasive treatment of white spot enamel lesions", Quintessence International, 38(8):633-636 (Sep. 2007).

Aytepe, Z., et al., "Effect of CCP-ACP on oral health of cerebral palsy children", Abstract 3343, Toronto, Canada. (Jul. 2008).

Bavetta et al., "Protein Factors and Experimental Rat Caries", Nutr. 63:107-117 (1957).

(Continued)

*Primary Examiner* — Satyanarayana R Gudibande (74) *Attorney, Agent, or Firm* — Merchant & Gould P.C.

(57) ABSTRACT

The present invention provides a phosphopeptide or phosphoprotein (PP) stabilised amorphous calcium phosphate or amorphous calcium fluoride phosphate complex having a calcium ion greater than about 30 moles of calcium per mole of PP.

11 Claims, 2 Drawing Sheets

(56) References Cited

OTHER PUBLICATIONS

Biesbrock, Aaron R., "Relative anti-caries efficacy of 1100, 1700, 2200, and 2800 ppm fluoride ion in a sodium fluoride dentifrice over 1 year", Community Dentistry and Oral Epidemiology, 29:382-389 (2001).

Biesbrock, A.R., et al., "Reversal of Incipient and Radiographic Caries Through the Use of Sodium and Stannous Fluoride Dentifrices in a Clinical Trial", The Journal of Clinical Dentistry, 9(1):5-10 (Feb. 1998).

Biesbrock, A. R. et al., "Dose response efficacy of sodium fluoride dentifrice at 9 and 21 months with supervised brushing", American Journal of Dentistry, 16(5) (Oct. 2003).

Black, et al., "Mottled Teeth: An endemic developmental imperfection of the enamel of the teeth heretofore unknown in the literature of dentistry", The Dental Cosmos, LVIII(2): 129-156 (Feb. 1916).

Burwell, A.K. et al., "Quantitative Tubule Occlusion in an in Vitro Remineralization/Demineralization Model", Abstract 0568, EADR, Dublin, Ireland (2006).

Burwell, A.K. et al., "Dentifrice Protection Against Dentin Demineralization in an in Vitro Study", Abstract 1764, IADR, New Orleans, USA. (2007).

Cai et al., "Remineralization of Enamel Subsurface Lesions in Situ by Sugar-Free Lozenges Containing Casein Phosphopeptide-Amorphous Calcium Phosphate", Aus. Dent. J. 48(4):240-3. (2003).

Cai, F. et al., "Remineralization by chewing gum containing CPP-ACP and citric acid." Abstract 190—84th General Session of the IADR, Brisbane, Australia (Jun. 28,-Jul. 1, 2006).

Cai, F. et al., "Effect of Addition of Citric Acid and Casein Phosphopeptide-Amorphous Calcium Phosphate to a Sugar-free chewing gum on Enamel Remineralization in Situ", Caries Research, 41:377-383 (2007).

Carrillo B. J., et al., "Nuevos avances tecnológicos en Odontologia Conservadora", La Gaceta Dental, 193:213, 218-219; English Abstract (Jun. 2008).

Chalmers, J. et al., "Minimal Intervention Dentistry in the New Millennium", DDS, Ms. Dentaltown, pp. 54 (Feb. 2008).

Chelariu, C., et al., "Nuove prospettive nella prevenzione della carieCongresso Nazionale del Collegio dei Docenti di Odontoiatria Roma", Poster session, published by "Doctor Os", No. 3, Mar. 2006. English Abstract (Apr. 5-7, 2006).

Chalmers, J.M., "Minimal intervention dentistry: part 1. Strategies for addressing the new caries challenge in older patients", Journal Can. Dental Association, 72(5):427-433 (Jun. 2006).

Chen, L. et al., "Calcium Release and Mechanical Properties of Experimental Calcium-Releasing Composites", Abstract 2572, IADR, New Orleans, USA (2007).

Cipolla, M. et al., "Fluoride and Calcium-Phosphate Effects on Fracture Toughness of Bleached Dentin", Abstract 1032, Toronto, Canada (Jul. 2008).

Coates, Liz, "Tooth mousse shows some unexpected beneficial side effects", Dental Asia (Nov./Dec. 2004).

Cochrane, N.J. et al., "QLF and TMR analysis of CPP-ACFP remineralized enamel in vitro", Abstract 192—84th General Session of the IADR, Brisbane, Australia (Jun. 28,-Jul. 1, 2006).

Cross K.J., et al., "Cation-Dependent Structural Features of Beta-Casein- (1-25)", Biochem. J. 356:277-86. (May 15, 2001).

Cross, K.J., et al., "Structural Studies of the β-Casein Phosphopeptide Bound to Amorphous Calcium Phosphate", IADR, General Session, Chiba, Abstract 0490, (2001).

Cross, K.J., et al., "Ultrastructural Studies of the Casein Phosphopeptide-Amorphous Calcium Phosphate Nanoclusters", IADR, General Session, Chiba, Abstract 0491, (2001).

Cross, K.J., et al., "NMR Studies of a Novel Calcium, Phosphate and Fluoride Delivery Vehicle-The Multiphosphorylated Peptide Alpha 51-Casein (589-79) Complexed with Amorphous Calcium Fluoride Phosphate", Biomaterials. Accepted for publication, (Jan. 2004).

Cross, K. J., et al. "Physicochemical Characterization of Casein Phosphopeptide-Amorphous Calcium Phosphate Nanocomplexes", The Journal of Biological Chemistry, 280(15):15362-15369 (Apr. 15, 2005).

Cross, K.J., et al., Structure and [15]N-Dynamics of casein phosphopeptide-amorphous calcium phosphate nanocomplexes. 84th General Session of the IADRBrisbane, Australia, Abstract 2534 (Jun. 28,-Jul. 1, 2006).

Cross, K.J., et al., "Casein Phosphopeptides in Oral Health—Chemistry and Clinical Applications", Current Pharmaceutical Design, 13:793-800 (2007).

Cross, K.J, et al. "Structural Characterization of anticariogenic casein Phosphopeptide alphas2 casein (46-70) complexed with amorphous calcium phosphate", Australian Dental Journal ADRF Special Research Supplement, 52(4):S10-S11 (2007).

Cross, K.J., et al., "Structural Characterization of β-Casein(1-25)-ACFP Complex.", Australian Dental Journal ADRF Special Research Supplement, 52(4):S12 (2007).

Cross K.J., et al. "Casein Phosphopeptide-Amorphous Calcium Phosphate Nanocomplexes: A Model of the Casini Micelle Core", Centre for Oral Health Science, School of Dental Science, The University of Melbourne, pp. 1-42 (Aug. 2008).

Curnow M.M.T., et al., "A Randomised Controlled Trial of the Efficacy of Supervised Toothbrushing in High—Caries-Risk Children."Carie Research, 36:294-300 (2002).

Davies G.M., "A randomized controlled trial of the effectiveness of providing free fluoride toothpaste from the age of 12 months on reducing caries in 5-6 year old children." Community Dental Health 19:131-136 (2002).

Deangelis et al., "Molecular of Anticariogenic Casein Phosphopeptide AS2-CN (2-20) NMR Spectroscopy Derived Constraints", Abstract 2997-82nd General Session of the IADR, Honolulu, Hawaii. (2004).

DenBesten, P.K. et al., "Biological Mechanisms of Fluorosis and Level and Timing of Systemic Exposure to Fluoride with Respect to Fluorosis." J. Dent Re 71(5):1238-1243 (May 1992).

Donovan, T., "Protocol for the prevention and management of root caries", Journal Compilation, 20(6):405-411 (2008).

Duckworth, R.M. "Oral Fluoride Measurements for Estimation of the Anti-caries Efficacy of Fluoride Treatments." J Dent Res. Apr. (1992).

Duckworth, R.M. "Effects of Mouthwashes of Variable NaF Concentration but Constant NaF Content on Oral Fluoride Retention", Caries Research, 18:43-47 (1994).

Featherstone, J.D., et al., "An in situ model for simultaneous assessment of inhibition of demineralization and enhancement of remineralization", Journal of Dental Research, (Spec Iss) 71:804-810 (Apr. 1992).

Feinmann, J., "This won't hurt a bit.", The Times, Saturday, Mar. 12, 2005.

Fejerskov et al., "Dental fluorosis—a handbook for health workers", Munksgaard, Copenhagen (1988).

Fejerskov et al., "The Nature of Mechanisms of Dental Fluorosis in Man", Journal of Dental Research, (Spec Iss) 69:692-700 (Feb. 1990).

Fejerskov, et al., "Posteruptive changes in human dental fluorosis—a histological and ultrastructural study", Pro Finn Dent. Soc., 87(4) (1991).

Fejerskov et al., "Fluoride in Dentistry 2nd edition." Munksgaard, Copenhagen (1996).

Ferrazzano, G.F., et al., "Nuove strategie nella prevenzione della carie dentaria:studio sperimentale sui caseino-fosfopeptidi." Prevenzione Odontostomatologica, Quintessenza Edizioni, 4:15-21, English Abstract (2005).

Ferrazzano, G.F., et al. "New Strategies in dental caries prevention: experimental study on casein phosphopetide.", European Journal of Paedetric Dentistry, 4:183-187 (2007).

Ferrazzano, G., et al., "Protective effect of yogurt extract on dental enamel demineralization in vitro", Australian Dental Journal, 53:314-319 (2008).

Freml, L. et al., "Efficacy of Hypersensitivity Agents on Demineralization under Provisional Crowns" Abstract 1346, IADR, New Orleans, USA (2007).

Fuller, B.L., et al., "Efficacy of MI Paste in Preventing Demineralization in Overdenture Abutments", Abstract 0503, IADR, New Orleans, USA (2007).

(56) References Cited

OTHER PUBLICATIONS

Gandolfi, M.G., et al., "Calcium silicate coating derived from Portland cement as treatment for hypersensitive dentine", Journal of Dentistry, 36:565-578 (2008).
Giambro, N.J. et al., "Characterization of Fluorosed Human Enamel by Color Reflectance, Ultrastructure, and Elemental Composition." Caries Res., Issue 29:251-257 (1995).
Giniger et al., "A 180-Day Clinical Investigation of the Tooth Whitening Efficacy of a bleaching Gel with Added Amorphous Calcium Phosphate." Journal of Clinical Dentistry. vol. XVI(1):11-16 (2005).
Giniger et al., "The clinical performance of professionally dispensed bleaching gel with added amorphous calcium phosphate." JADA, 136:383-392 (2005).
Gugnani, S., et al., "Comparative evaluation of two commercially available desensitising agents after scaling and root planning: an in vivo stud", PERIO, 5(2):121-129 (2008).
Haderlie, D.D. et al., "MI Paste and Fluoride effects on Secondary Caries", Abstract 0504, IADR, New Orleans, USA (2007).
Harper et al., "Cariostatic Evaluation of Cheeses with Diverse Physical and Compositional Characteristics", Caries Res. 20:123-130 (1986).
Harper et al., "Modification of Food Cariogenicity in Rats by Mineral-Rich Concentrates from Milk", J. Dent Res. 66:42-45 (1987).
Hartshone, JE. "The relationship between plaque index scores, fluoride content of plaque, plaque pH, dental caries experience and fluoride concentration in drinking water in a group of primary school children." Journal of the Dental Association of South Africa, 49:5-10 (1994).
Hay et al., "A Clinical Trial of the Anticaries Efficacy of Casein Derivatives Complexed with Calcium Phosphate in Patients with Salivary Gland Dysfunction", Oral. Surg. Oral Med Oral. Pathol Oral Radiol. Endod. (2002); 93:271-275.
Hicks, J., et al. "Biological factors in dental caries: role of remineralization and fluoride in the dynamic process of demineralization and remineralization (part 3)." The Journal of Clinical Pediatric Dentistry. 28(3): (2004).
Hicks, J., et al., "Casein Phosphopeptide-Amorphous calcium phosphate paste: root surface caries formation", Abstract 3275—IADR, Baltimore, Maryland, USA (Mar. 2005).
Holler, B. E. et al., "Fluoride uptake and distribution in enamel and dentin after application of different fluoride solutions", Clin Oral Invest, 6:137-144 (2002).
Holloway et al., "Effects of Various Sucrose-Casein Ratios in Purified Diets on the Teeth and Supporting Structures of Rats", Arch Oral Biol. 3:185-200 (1961).
Holt et al., "Ability of a β-casein Phosphopeptide to modulate the precipitation of calcium phosphate by forming amorphous dicalcium phosphate nanoclusters", Biochem. J., 314:1035-1039 (1996).
Holt, Carl, "An equilibrium thermodynamic", Euro. Biophysics J., pp. 421-434 (2004).
Huang, A., et al., "Remineralization of eroded teeth using CPP-ACP paste", Abstract 3267, Toronto, Canada. (Jul. 2008).
Huq, N.L., et al., "A H-NMR study of the casein Phosphopeptide αs1-casein(59-79)," Biochimica et biophysica Acta 1247:201-208 (1995).
Huq, N.L., et al., "Molecular Modeling of the Multiphosphorylated Sequence Motif Bound to Hydroxyapatite Surfaces" (59-79), Journal Mol. Mod. 6:35-47 (2000).
Huq, N.L., et al., "Nascent Helix." Journal of Peptide Science, pp. 386-392, (2003).
Huq, N.L., et al., "Molecular Modelling of the Multiphosphorylated Casein Phosphopeptide Alpha S1-Casein (59-79) based on NMR constraints", Journal of Dairy Research, 71:1-5 (2004).
Iijima et al., "Acid Resistance of Enamel Subsurface Lesions Remineralized by a Sugar-Free Chewing Gum Containing Casein Phosphopeptide-Amorphous Calcium Phosphate (CPP-ACP)", Caries, Research, 38:551-556 (2004).
Iijima, Y. et al., "Acid resistance of remineralized enamel by a sugar-free chewing gum", Abstract 184—84th General Session of the IADR, Brisbane, Australia (Jun. 28,-Jul. 1, 2006).
Inaba, D., et al. "Effect of Sodium Hypochlorite Treatment on Remineralization of Human Root Dentine in vitro." Caries Research, 30:218-224 (1996).
Inaba, D., et al. "Intraoral changes in NaOCl-treated Root Dentin Lesions: A Pilot Study.", Journal of Dental Health, 50:824-826 (2000).
Kandelman D., et al., "A 24-month clinical study of the incidence and progression of dental caries in relation to consumption of chewing gum containing xylitol in school preventive programs", Journal Dent Res vol. 69(11):1771-1775 (1990).
Kariya et al., "Fluoride Effect on Acid Resistance Capacity of CPP-ACP Containing Material", Abstract 2045-82nd General Session of the IADR, Honolulu, Hawaii (2004).
Kariya, S. et al., "Remineralization of enamel lesion by a novel cream with both CPP-ACP and fluoride", Poster session 136—54th Annual ORCA Congress (2007).
Kecik, D. et al., "Effect of Acidulated Phosphate Fluoride and Casein Phosphopeptide-Amorphous Calcium Phosphate Application on Shear Bond Strength of Orthodontic Brackets", Angle Orthodontist, 78(1):129-133 (2008).
Khan, S., "White Spots on Teeth", Buzzle.com Intelligent Life on the Web (Jan. 2010).
Kim, K., et al., "Remineralization of the artificial caries lesion using CPP-ACP and fluoride", Abstract 3280, Toronto, Canada. (Jul. 2008).
Kowalczyk et al., "Evaluation of the product based on Recaldent™ technology in the treatment of dentin hypersensitivity", Advances in Medical Sciences, suppl 1, 51:40-42, (2006).
Krobicka et al., "The Effects of Cheese Snacks on Caries in Desalivated Rats", Journal of Dental Research, 66:1116-1119, (1987).
Kumar, VLN et al., "The effect of casein phosphopeptide-amorphous calcium phosphate on remineralization of artificial caries-like lesions: an in vitro study", Australian Dental Journal, 53:34-40 (2008).
Larsson, K., Skold, et al. "Fluoride concentration in plaque in adolescents after topical application of different fluoride varnishes." Clin Oral Invest 4:31-34 (2000).
Lasfargues, J., et al., "La reminéralisation des lésions carieuses (2) synergies thérapautiques", Realités Cliniques, 15(3):261-275 261-275. English Abstract (2004).
Legeros, R.Z., "Calcium phosphates in demineralization/remineralization processes." Journal of Clinical Dentistry, 10:65-73 (1999).
Lewis, J., "Brush, floss and mousse?" Women Dentistry Journal, 2(4):18-19 (Winter 2005).
Little, Elaine et al., "An equilibrium thermodynamic." Euro Biophysics J. 33:435-447 (2004).
Loesche W.J., "Role of streptococcus mutans in human dental decay", Microbiological Reviews, 50(4):353-380 (Dec. 1986).
Lynch, R.J., et al, "Low-Levels of Fluoride in plaque and saliva and their effect on the demineralization and remineralisation of enamel; role of fluoride of toothpastes." International Dental Journal, 54(5):304-309 (2004).
Malcmacher, L., "Enamel Remineralization: The Medical Model of Practicing Dentistry", Dentistry Today (Nov. 2006).
Malcmacher, L., "Vitamins for teeth", Common Sense Dentistry pp. 130 and 144 (Oct. 2006).
Manton, D.J., et al. "In situ remineralisation by sugar-free gums, one containing CPP-ACP", Abstract 0020—45th Annual Meeting of Australian/New Zealand Division of the IADR (Sep. 25-28, 2005).
Manton, D.J., "Promoting remineralization: using casein phosphopeptide—stabilized amorphous calcium (fluoride) phosphate. A chemical approach." EAPD, Amsterdam (Jun. 8-11, 2006).
Manton, D. J., et al., "Remineralization of white spot lesions in situ by tooth mousse." Abstract 185—84th General Session of the IADR, Brisbane, Australia (Jun. 28,-Jul. 1, 2006).
Manton, D. et al. "Effect of ozone and Tooth Mousse™ on the efficacy of peroxide bleaching", Australian Dental Journal, 53:128-132 (2008).
Manton, D., "Dental Caries: Where to From Here?", Ann Roy Austral Coll Dent Surg., 19:73-76 (May-Jun. 2008).

(56) References Cited

OTHER PUBLICATIONS

Manton, D., et al., "Remineralization of enamel subsurface lesions in situ by the use of three commercially available sugar-free gums", International Journal of Paediatric Dentistry, 18:284-290 (2008).
Mazzaoui, S.A., et al.,"Incorporation of Casein Phosphopeptide-Amorphous Calcium Phosphate into a Glass-ionomer Cement," Journal of Dental Research 82(11):914-918 (2003).
Melkers, M.J. "Keeping focused on the finish line. Accomplishing goals with traditional and progressive technologies", Dentaltown, 5(11):60, 62, 64&66 (2004).
Mickenautsch, S., "An Introduction to Minimal Intervention Dentistry (MI)", Dental News, vol. XIV(IV):13-20 (2007).
Milnar, F.J. "Considering biomodification and remineralization techniques as adjuncts to vital tooth-bleaching regimens", Compendium, 28(5):234-240 (2007).
Minami et al., "Effects of Cheese and Milk Containing CPP-ACP on Enamel Remineralization", 2049-82nd General Session of the IADR, Honolulu, Hawaii, Abstract only (2004).
Misra, S. et al. "Early Childhood Caries—A Review", Dental Update, 34:556-564 (2007).
Miyazaki, M. et al., "Using ultrasound transmission velocity to analyze demineralization of tooth substrate" Abstract 94—52nd ORCA Congress, Indianapolis, USA/Caries Research, 39:319 (Jul. 2005).
Morgan, M.V., et al., "CPP-ACP gum slows progression and enhances regression of dental caries" Abstract 2445—84th General Session of the IADR, Brisbane, Australia (Jun. 28,-Jul. 1, 2006).
Morgan, M.V., et al., "The Anticariogenic Effect of Sugar-Free Gum Containing CPP-ACP Nanocomplexes on Approximal Caries Determined Using Digital Bitewing Radiography.", Caries Research, 42:171-184 (2008).
Morgan, M.V., et al., "Clinical trial of tooth mousse on white spot lesions", Cooperative research centre for oral health science. Toronto, Briefing Paper No. 2 (2008).
Morgan, MV et al., "A Clinical Trial Measuring White Spot Lesion Progression and Regression", Abstract 0112, Toronto, Canada (Jul. 2008).
Moule, C.A., et al. "Resin bonding using an all-etch or self-etch adhesive to enamel after carbamide peroxide and/or CPP-ACP treatment", Australian Dental Journal, 52(2):133-137 (2007).
Mount, G.J., "A new paradigm for operative dentistry.", Australian Dental Journal 52(4):264-270 (2007).
Murata et al., "Remineralization Power by Xylitol Chewing Gums", Abstract 2046-82nd General Session of the IADR, Honolulu, Hawaii. Abstract only (2004).
Narayana, T., et al., "An in vitro study of wear prevention in dentine", Abstract 2424—84th General Session of the IADR, Brisbane, Australia (Jun. 28,-Jul. 1, 2006).
Ng, H. et al. "Aesthetic management of severely fluorosed incisors in an adolescent female." Australian Dental Journal, 52(3):243-248 (2007).
O'Hehir, T., "Caries—More than a filling", Hygienetown Magazine Hygientown.com, pp. 8-12 (Jul./Aug. 2008).
Oshiro, M., et al., "Effect of CPP-ACP paste on tooth mineralization: an FE-SEM study", Journal of Oral Science, 49(2):115-120 (2007).
Perdigao, J., et al., "Contemporary Trends and Techniques in Tooth Whitening: A Review", Practical Procedures & Aesthetic Dentistry, 16(3):185-192 (2004).
Perich, J.W., et al., "Efficient Solution-Phase Synthesis of Multiple O-Phosphoseryl-Containing Peptides Related to Casein and Statherin", Int. J. Pept. Protein Res. 40(2):81-88 (Aug. 1992).
Perich et al., "The Use of Synthetic Phosphopeptides for Epitope Mapping of the AS1-Casein Phosphopeptide Segment 59-70", Bioorg. Med. Chem. Lett. 2:1153-1154 (1992).
Peschke, J.C. et al. "Nucleating Ability of Calcium Phosphate-Protein-Composites.", Abstract 2244, IADR, New Orleans, USA (2007).
Piekarz, C. et al. "An in vitro assessment of the role of Tooth Mousse in preventing wine erosion.", Australian Dental Journal, 53:22-25 (2008).
Pietrzycka, K., "Chemical methods of treatment of dental caries: the action and application of CPP-ACP.", E-Dentico, 2(18):68-74, English Abstract (2008).
Pitts, N.B., "Are we ready to move from operative to non-operative/preventive treatment of dental caries in clinical practice?", Caries Research, 38:294-305 (2004).
Plate, U., et al., Investigation of the early mineralization on collagen in dentine of rat incisors by quantitative electron spectroscopic diffraction (ESD), Cell Tissue Research, 278:543-547 (1994).
Poitevin et al., "Clinical Effectiveness of a CPP-ACP Crème for Tooth Hypersensitivity Treatment", EADR Istanbul, Abstract 0136 (Aug. 24-28, 2004).
Quartarone, E., et al., "Surface kinetic roughening caused by dental erosion: an atomic force microscopy study", Journal of Applied Physics, 103(104702):1-6 (2008).
Rahiotis, C., et al. "Effect of a CPP-ACP agent on the demineralization and remineralization of dentine in vitro", Journal of Dentistry, 35:695-698 (2007).
Rahiotis, C. et al., "Characterization of oral films formed in the presence of a CPP-ACP agent: An in situ study", Journal of Dentistry, 36:272-280 (2008).
Ramadas, Y., "The oral care for children with malignancies.", Synopses; Synopses: The Newsletter of the Australian and New Zealand Society of Paediatric Dentistry, Winning 2003 Postgraduate Essay, Issue 28:1-20 (Mar. 2004).
Ramalingam et al., "An in Vitro Investigation of the Effects of Casein Phosphopeptide-Stabilized Amorphous Calcium Phosphate (CPP-ACP) on Erosion of Human Dental Enamel by a Sports Drink", IADR, General Session, San Diego Abstract 2810 (2002).
Ramalingam et al., "Erosion of Human Dental Enamel by Sports Drinks", Synopses 27:16-19, (2003).
Ramalingam, L. et al., "Adding Caesin Phosphopetide-amorphous Calcium Phosphate to Sports Drinks to Eliminate In Vitro Erosion", Pediatric Dentistry, 27(1):61-67 (2005).
Ranjitkar, S., et al., "Enamel wear prevention under conditions simulating bruxism and acid regurgitation", Abstract 2428—84th General Session of the IADR, Brisbane, Australia (Jun. 28,-Jul. 1, 2006).
Ranjitkar, S. et al., "The Role of Tooth Mousse in preventing enamel wear.", Poster 0375—session 39—42nd annual meeting of IADR-Continental European and Israeli Divisions, Sep. 26-29, (2007).
Ranjitkar, S., et al., "The role of tooth mousse in reducing erosive tooth wear", Abstract 2500, Toronto, Canada. (Jul. 2008).
Rees, J., et al., "Pronamel and tooth mousse: An initial assessment of erosion prevention in vitro", Journal of Dentistry, 35:355-357 (2007).
Reeves, "Calcium Phosphate Sequestering Phosphopeptide from Casein", Latour NG. Science 128:472 (1958).
Reich, E. "Das kleine gewisse Etwas zur Remineralisation", Zahnmedizin, English Abstract 95(21):2-9 (2005).
Reich, E. "Flüssiger Zahnschmelz." Dental Magazine, English Abstract (Feb. 2005).
Reich, E. Dental Products Report Europe (Downloaded on May 30, 2006 http://www.dpreurope.com) (Jan. 1, 2006).
Reich, E., "GC Tooth Mousse—Ein neuer Ansatz zur Remineralisation", Kongress: Wissenschaft und Praxis der Sanften Zahnheilkunde, Lindau am Bodensee, English Abstract (Mar. 3-4, 2006).
Reich, E., "Die Betreuung von Kariespatienten in der Praxis", Quintessenz, 59(12):1301-1307, English Abstract (2008).
Reynolds, E.C., et al., "A Review of the Effect of Milk on Dental Caries", Aust. J. Dairy Tech., 34:175-179 (1979).
Reynolds, E.C., et al., "Effect of Milk on Caries Incidence and Bacterial Composition of Dental Plaque in the Rat", Arch Oral Biol. 26(5):445-451 (1981).
Reynolds, E.C., et al., "Phosphoprotein Inhibition of Hydroxyapatite Dissolution", Calcif. Tissue Int. 34 Suppl. 2:S52-6. (1982).
Reynolds, E.C., et al., "Effect of Adsorbed Protein on Hydroxyapatite Zeta Potential and Streptococcus Mutans Adherence", Infect. Immun. 39(3):1285-1290. (Mar. 1983).
Reynolds, E.C., et al., "Effect of Casein and Whey-Protein Solutions on Caries Experience and Feeding Patterns of the Rat", Arch Oral Biol. 29(11):927-33. (1984).

(56) References Cited

OTHER PUBLICATIONS

Reynolds, E.C., et al., "Reduction of Chocolate's Cariogenicity by Supplementation with Sodium Caseinate", Caries Res. 21(5):445-51. (1987).
Reynolds, E.C., et al., "Confectionery Composition and Rat Caries", Caries Res. 21(6):538-45. (1987).
Reynolds, E.C., "The Prevention of Sub-Surface Demineralization of Bovine Enamel and Change in Plaque Composition by Casein in an Intra-Oral Model", J. Dent. Res. 66(6):1120-1127. (Jun. 1987).
Reynolds, E.C., et al., "Protein Dissimilation by Human Salivary-Sediment Bacteria", J. Dent. Res. 68:124-29 (1989).
Reynolds, E.C., et al., "Cariogenicity of a Confection Supplemented with Sodium Caseinate at a Palatable Level", Caries Res. 23:368-70 (1989).
Reynolds, E.C., et al., "A Selective Precipitation Purification Procedure for Multiple Phosphoseryl-Containing Peptides and Methods for Their Identification", Anal. Biochem., 217(2):277-84. (Mar. 1994).
Reynolds, E.C. "Dairy Products and Dental Health." Proceedings of the Nutrition Society of Australia, 19:95-102 (1995).
Reynolds, E.C., et al., "Anticariogenicity of Calcium Phosphate Complexes of Tryptic Casein Phosphopeptides in the Rat", Journal of Dental Research 74(6):1272-9 (Jun. 1995).
Reynolds, E.C., "Remineralization of Enamel Subsurface Lesions by Casein Phosphopeptide-stabilized Calcium Phosphate Solutions," J Dent Res 76(9):1587-1595, Sep. (1997).
Reynolds EC "Dairy products and dental health." Proc Nutr Soc Aus, 19:95-102 (1995).
Reynolds, E.C., "Anticariogenic." J. of Sp. Care in Dentistry, vol. 18(1):8-16 (1998).
Reynolds, E.C., et al., "Advances in Enamel Remineralization: Anticariogenic Casein Phosphopeptide-Amorphous Calcium Phosphate", J. Clin. Dent. X(2):86-88. (1999).
Reynolds, E.C., "Anticariogenic Casein Phosphopeptides", Prot. Peptide Lett. pp. 295-303. (1999).
Reynolds, E.C., "The Role of Phosphopeptides in Caries Prevention", Dental Perspectives 3:6-7. (1999).
Reynolds, E.C., et al., "Enamel Remineralization by Chewing Gum Containing Casein Phosphopeptide-Amorphous Calcium Phosphate", IADR, General Session, Chiba, Abstract 0489 (2001).
Reynolds EC "Health aspects of dairy products—Dairy products in relation to caries prevention and oral health." Invited review. Encycl Dairy Sciences (2001).
Reynolds, E.C., "Remineralization of early enamel caries by anticariogenic casein phosphopeptide-amorphous calcium phosphate nanocomplexes" Dental Practice (Nov./Dec. 2001).
Reynolds, E.C., "Caries Prevention and Oral Health", Health Aspects of Dairy Products/Caries Prevention and Oral Health, Elsevier Science Ltd, pp. 1306-1313 (2002).
Reynolds, E.C., "Dairy Components in Oral Health", Aust. J. Dairy Tech. 58:79-81 (2003).
Reynolds, E.C. et al., "Retention in Plaque and Remineralization of Enamel Lesions by Various Forms of Calcium in a Mouthrinse or Sugar-free Chewing Gum," Journal of Dental Research, 82(3):206-211 (2003).
Reynolds, E.C., t al. "Additional Aids to the Remineralisation of Tooth Structure," Preservation and Restoration of Tooth Structure, Chapter 8, Knowledge Books & Software, 111-118, (2005).
Reynolds, E.C., et al., "Improved plaque uptake and enamel remineralization by fluoride with CPP-ACP." Abstract 2538—84th General Session of the IADR, Brisbane, Australia. (Jun. 28,-Jul. 1, 2006).
Reynolds, E.C., "Calcium phosphate-based remineralization systems: scientific evidence?" Australian Dental Journal, 53:268-273 (2008).
Reynolds, EC et al. "Fluoride and casein phosphopeptide-amorphous calcium phosphate", J Dent Res 87(4):344-348 (2008).
Rini Sudjalim, T. et al., "Prevention of demineralization around orthodontic brackets in vitro", American Journal of Orthodontics and Dentofacial Orthopedics, 131(6):705.E1-705.E9 (2007).
Roberts, "Role of Models in Assessing New Agents for Caries Prevention—Non-Fluoride Systems", Adv. Dent. Research, 9(3):304-311; discussion 312-4 (Nov. 1995).
Roberts, M.J., et al., "Remineralisation of fluorotic enamel lesions by casein phosphopeptide—amorphous calcium fluorophosphate (CPP-ACFP) solution." IADR, ANZ division, Abstract 54 (2000).
Robinson et al. "Effect of Surface Zone Deproteinisation on the Access of Mineral Ions into Subsurface Carious Lesions of Human Enamel", *Caries Research*; 24:226-230 (1990).
Rose, "Binding Characteristics of Streptococcus Mutans for Calcium and Casein Phosphopeptide", Caries. Research, 34:427-431 (2000).
Rose, "Effects of an Anticariogenic Casein Phosphopeptide on Calcium Diffusion in Streptococcal Model Dental Plaques", Arch Oral Biol, 45(7):569-575 (2000).
Rosen et al., "Effect of Cheese, With and Without Sucrose, on Dental Caries and Recovery of Streptococcus Mutans in Rats", Journal of Dental Research, 633:894-96 (1984).
Rozwadowska, E., "Children and private dentistry" Private Dentistry, Special Issue, pp. 109-113 (May 2006).
Sakaguchi, Y., et al., "Preventing acid induced enamel demineralization using CPP-ACP containing paste" Abstract 2055—IADR, Baltimore, Maryland, USA (Mar. 2005).
Sakaguchi, Y. et al., "Remineralization potential of CPP-ACP and its synergy with fluoride", Abstract 191—84th General Session of the IADR, Brisbane, Australia (Jun. 28,-Jul. 1, 2006).
Sato et al., "Caries prevention Potential of a Tooth-coating Material Containing Casein Phosphopeptide-Amorphous Calcium Phosphate (CPP-ACP)", IADR, General session, Goteborg, Abstract 1007 (2003).
Schüpbach et al., "Incorporation of Caseinoglycomacropeptide and Caseinophosphopeptide into the Salivary Pellicle Inhibits Adherence of Mutans Streptococci", Journal of Dental Research, 75:1779-1788 (1996).
Schweigert, B.S., et al., "Dental caries in the cotton rat. VI. The effect of the amount of protein, fat and carbohydrate in the diet on the incidence and extent of carious lesions", Journal of Nutrition, 31:439-447 (1946).
Shaw, J.H., "Effects of dietary composition on tooth decay in the albino rat" Journal of Nutrition 41:23-24 (1950).
Sheharyar, S., et al., "Efficacy of MI Paste for Sensitivity Associated With Vital Bleaching", Abstract 2041, IADR, New Orleans, USA (2007).
Shen et al., "Remineralization of Enamel Subsurface Lesions by Sugar-free Chewing Gum Containing Casein Phosphopeptide-Amorphous Calcium Phosphate," J Dent Res 80(12):2066-2070 (2001).
Shen, P., et al., "Enamel remineralization by a mouthrinse containing casein phosphopeptide-amorphous calcium phosphate and fluoride in an in situ model" Australian Dental Journal ADRF Special Research Supplement, 49(4):S19 (2004).
Shen, P., et al., "Remineralization by a mouthrinse containing CPP-ACP at pH 5.5", Abstract 189—84th General Session of the IADR, Brisbane, Australia (Jun. 28,-Jul. 1, 2006).
Shen. P. et al. "Remineralization of Enamel." The Univ. of Melbourne. Research Reports. pp. 266-270.
Silva, M.F. et al., "Effects of Water-soluble Components of Cheese on Experimental Caries in Humans," J Dent Res 66(1):38-41 (Jan. 1987).
Silva, Margarita et al. "Fluoride content of infant formulae in Australia", Australian Dental Journal 41:1 (1996).
Slomiany, B. et al., "Salivary Mucins in Oral Mucosal Defense", Gen. Pharmac., 27(5):761-771 (1996).
Smith, S., et al., "Ultramorphological evaluation of dentin after treatment with different desensitizing agents", Abstract 0941, IADR, New Orleans, USA (2007).
Smolenski, D., et al., "MI Paste and Fluoride for Caries Prevention In-Vitro", Abstract 0505, IADR, New Orleans, USA (2007).
Steinberg, S., "A modern paradigm for caries management, Part 1: Diagnosis and Treatment." Dentistry Today, (Downloaded on Mar. 1, 2007, http://www.dentistrytoday.net) (Feb. 2007).
Steinberg, S., "A modern paradigm for caries management, Part 2: A practical protocol." Dentistry Today (Downloaded on Jul. 1, 2007, http://www.dentistrytoday.net) (Jun. 2007).

(56) References Cited

OTHER PUBLICATIONS

StiiBer, L., "Kariesprotektive Eigenschaften des durch Caseinphosphopeptid stabilisierten amorphen Calciumphosphat-Nanokomplexes (CPP-ACP)", Deutsche Zahnarztliche Zeitschrift, 82 Abstract (Sep. 2007).
Sudjalim, T.R., et al., "Prevention of white spot lesions in orthodontic practice: a contemporary review", Australian Dental Journal, 51(4):284-289 (2006).
Sukasaem, H., et al., "Effect of CPP-ACP on hardness of enamel eroded by Cola-drink." Abstract 1673—84th General Session of the IADR, Brisbane, Australia (Jun. 28,-Jul. 1, 2006).
Talbo et al., "MALDI-PSD-MS Analysis of the Phosphorylation Sites of Caseinomacropeptide", Petides 22(7):1093-1098. (Jul. 2001).
Takamizawa, T., et al., "Determination of demineralization of tooth substrate by use of an ultrasonic device." Japan J Consery Dent 47(24) Spring Issue—Abstract B-4, (Jun. 2004).
Tantbirojn, D. et al., "Changes in surface hardness of enamel by a cola drink and CPP-ACP paste", Journal of Dentistry, 36:74-79 (2008).
Ten Cate, Jacob M., "Current concepts on the theories of the mechanism of action of fluoride", ACTA ODONTOL, SCAND 57 (1999).
Theerapiboon, U. et al., "Remineralization of artificial caries by CPP-ACP paste", Abstract 3274, Toronto, Canada. (Jul. 2008).
Trajtenberg, C.P. et al., "CPP-ACP Paste with Fluoride: In Vitro Root Surface Caries Formation", Abstract 0500, IADR New Orleans, USA (2007).
Turssi, C.P. et al., "Progression of erosion following use of calcium and phosphorus compounds", Abstract 2499, Toronto, Canada. (Jul. 2008).
Ung, M., et al., "Investigation of the binding of casein phosphopeptides to the major enamel pellicle proteins", Australian Dental Journal ADRF Special Research Supplement, 49(4):S19-S20 (2004).
Vladic, J., et al., "Combined CPP-ACP and photoactivated disinfection (PAD) therapy in arresting root surface caries: a case report", British Dental Journal, 203(8):457-459 (2007).
Walker, Glen et al., "Increased remineralization of tooth enamel by milk containing added casein phosphopeptide-amorphous calcium phosphate", Journal of Dairy Research pp. 74-78 (2006).
Walsh, L.J., et al., "Effect of CPP-ACP versus potassium nitrate on cervical dentinal hypersensitivity", Abstract 947—84th General Session of the IADR, Brisbane, Australia. (Jun. 28,-Jul. 1, 2006).
Walsh, L.J., "The effects of GC Tooth Mousse on cervical dentinal sensitivity: a controlled clinical trial", International Dentistry SA—Australasian Edition 5(1):16-23 (2007).
Walsh, L.J., "Application of the System for Total Environmental Management (STEM) to demineralization, dental erosion and tooth wear.", Australasian Dental Practice, pp. 52-58 (Jan.-Feb. 2008).
Weiss, Dr. V., "Kariesprophylaxe in der kinderzahnnärztlichen Praxis", ZWP, 18:7679. English Abstract (Oct. 2005).
Westerman, G., et al., "Argon Laser and Remineralizing Paste Effect on Root Surface Caries", Abstract 0018, IADR, New Orleans, USA (2007).
Westerman, G. et al., "The Argon Laser and Remineralizing Paste with Fluoride Effects on Enamel Caries", AAPD,Washington (2008).
White, "Use of Synthetic Polymer Gels for Artificial Carious Lesion Preparation", Caries Research 21, pp. 228-242. Abstract Only (1987).
Wilfershausen, B., et al., "In-Vitro- Studie Zur Überprüfung einermöglichen Remeralisation durch caesinphosphopetidhaltige Calciumphosphat-komplexe (CPP_ACP)", Deutsche Zahnärztiche Zeitschrift, 63(2):134-139. English Abstract (2008).
William, V., et al., "Molar Incisor Hypomineralization: Review and Recommendations for Clinical Management", Pediatric Dentistry, 28(3):224-232 (2006).
Wong, R., et al., "Incorporation of casein phosphopeptide-amorphous calcium phosphate into a temporary cement", Abstract 0653—84th General Session of the IADR, Brisbane, Australia (Jun. 28,-Jul. 1, 2006).
Wong, L., et al., "Plaque microcosm biofilm mineralization by CPP-ACP and calcium-phosphate-monofluorophosphate-urea mineralizing solution." Abstract 1269—84th General Session of the IADR, Brisbane, Australia (Jun. 28,-Jul. 1, 2006).
Wright, S. et al., "Artificial Caries Inhibited with MI Paste and Two Restorative Materials", Abstract 2777, IADR, New Orleans, USA (2007).
Xie, Q. et al., "Remineralization Effects of CPP-ACP and Proanthocyanidin on Artificial Root Caries", Abstract 0512, IADR, New Orleans, USA (2007).
Yamaguchi, K., et al., "Effect of CPP-ACP paste on mechanical properties of bovine enamel as determined by an ultrasonic device", Journal of Dentistry, 34:230-236 (2006).
Yamaguchi, K., et al., "Ultrasonic determination of the effect of casein phosphopeptide-amorphous calcium phosphate paste on the demineralization of bovine dentin", Caries Research, 41:204-207 (2007).
Zero, D.T. "In situ caries models." Advance Dent Research 9(3):214-230, discussion 231-234 (Nov. 1995).
Zhang, L, et al. "Experimental study of phosphopeptide in promoting tooth remineralisation." Chinese Journal of Dental Research., 3(1):27-30 (May 2000).
Zhao, Q-Z, et al. "The Remineralization for Enamel lesions by Casin Phosphopeptide-Amorphous Calcium phospate in vitro." Zhonghua Kou Qiang Yi Kxue Za Zhi. 36(6):421-423 (2002).
Caplus Copyright 2005. "NMR Studies of a Novel Calcium, Phosphate and Fluoride Delivery Vehicle <SYM97>$_{Sl}$-Casein (59-79) by Stabilized Amorphous Calcium Fluoride Phosphate Nanocomplexes".
"Caséin phosphopeptide et phosphate de calcium amorphe: un complexe prometteur", Dialogue Dentaire, /N°30, pp. 27-29 (Spring 2005). English Abstract provided.
"Colorimetry", CIE Technical Committee, Second Edition, CIE 1986.
Database WPI Week 200316, Thomason Scientific, London, GB; 2003-165149, XP002537968 & SE 0 100 558 A, Mediteam Dental AB, Aug. 21, 2002. Abstract.
"Editors' Choice—Prospec MI Paste." The Dental Advisor, 22(5) (Jun. 2005).
"GC stellt Kasein-haltige Zahnschutzcreme vor—Vorbeugen statt reparieren" DZW Special IDS-Nachlese, English Abstract (2005).
"GC Tooth Mousse—Eine ganz andere Art der Prävention." Dental Spiegel, pp. 53-54. English Abstract (Feb. 2005).
"Minimale Intervention für maximale Mundgesundheit.", DZW Special, English Abstract (Mar. 2005). "Preventive agents." The Dental Advisor, vol. 21(10):1-5 (Dec. 2004).
Minimum Intervention: modernes Kariesmanagement—Weg vom chirurgichen, hin zum medizinischen Versorgungsansatz mit GC. IDS-31$^{st}$ International Dental Show, Cologne, (Today—Independent Trade Show Daily—Saturday) (Apr. 12-16, 2005).
"Preventative Agents", the Dental Advisor 21(13) (Dec. 2004).
Products for the dental hygienist—Desensitizers. The Dental Advisor, vol. 23, No. 6, Jul./Aug. 2006.
"Putting mouths where the money is.", DPRAsia, Jan./Feb. 2007.
"Tooth Mousse: Pierre qui roule n'amasse pas mousse? Ben si!", Clinic—27:218 (Apr. 2006)—English Abstract provided.
"Tradition and modernes know how—ein Erfolgsrezept", Zahn Prax 8, 5:267 English Abstract (2005).
Translation of Russian Office Action from Application No. 2007123603, May 26, 2009.
International Search Report and Written Opinion for related PCT/AU2006/000885 mailed Sep. 25, 2006.

* cited by examiner

IONIC COMPLEXES

RELATED APPLICATIONS

This application is a Continuation Application of U.S. Ser. No. 11/917,395, filed 13 Dec. 2007, now U.S. Pat. No. 8,603,988, issued Dec. 10, 2013, which is a National Stage Application of PCT/AU2006/000885, filed 23 Jun. 2006, which claims benefit of U.S. Ser. No. 60/694,019, filed 24 Jun. 2005 and which applications are incorporated herein by reference. To the extent appropriate, a claim of priority is made to each of the above disclosed applications.

The present invention relates to superloaded complexes of amorphous calcium phosphate and/or amorphous calcium fluoride phosphate stabilised byphosphopetides/phosphoproteins. These superloaded complexes have anticariogenic properties useful to protect tooth and bone structures as they remineralize (repair) early stages of dental caries as well as other dental/medical applications (including anticalculus, anti-erosion/corrosion and anti-dentinal hypersensitivity). Methods of making the superloaded complexes of the invention and of treatment or prevention of dental caries, dental calculus, dental erosion/corrosion and dental hypersensitivity are also provided.

BACKGROUND

Dental caries is initiated by the demineralization of hard tissue of the teeth usually by organic acids produced from fermentation of dietary sugar by dental plaque odontopathogenic bacteria. Dental caries is still a major public health problem. Further, resfored tooth surfaces can be susceptible to further dental caries around the margins of the restoration. Even though the prevalence of dental caries has decreased through the use of fluoride in most developed countries, the disease remains a major public health problem. Dental erosion/corrosion is the loss of tooth mineral by dietary or regurgitated acids. Dental hypersensitivity is due to exposed dentinal tubules through loss of the protective mineralized layer, cementum and dental calculus is the unwanted accretion of calcium phosphate minerals on the tooth surface. All these conditions, dental caries, dental erosion/corrosion, dental hypersensitivity and dental calculus are therefore imbalances in the level of calcium phosphates. Dental caries, dental erosion/corrosion and dental hypersensitivity can be treated with stabilized amorphous calcium phosphate (ACP) by providing bioavailable calcium and phosphate ions to replace the lost calcium phosphate mineral. Stabilized ACP can also bind to the surface of dental calculus and prevent further accretion. Stabilized ACP and stabilized amorphous calcium fluoride phosphate (ACFP) therefore can play a major role in preventing and treating oral diseases and other medical conditions.

Casein is present in milk in the form of micelles, which are believed to be roughly spherical particles with a radius of about 100 nm, dispersed in a continuous phase of water, salt, lactose and whey proteins. The casein micelles serve as a carrier of calcium phosphate providing a bioavailable source of calcium and phosphate ions for bone and teeth formation. The ability of casein micelles to maintain calcium and phosphate ions in a soluble and bioavailable state is retained by the tryptic multiphosphorylated peptides of the caseins known as the casein phosphopeptides (CPP). WO 98/40406 describes casein phosphopeptide-amorphous calcium phosphate complexes (CPP-ACP) and CPP-stabilised amorphous calcium fluoride phosphate complexes (CPP-ACFP) which have been produced at alkaline pH. Such complexes have been shown to prevent enamel demineralization and promote remineralization of enamel subsurface lesions in animal and human in situ caries models.

The phosphopeptides which are active in forming the complexes do so whether or not they are part of a full-length casein protein. The active casein phosphopeptides (CPP) formed by tryptic digestion have been specified in U.S. Pat. No. 5,015,628 and include peptides Bos $\alpha_{s1}$-casein X-5P (f59-79) [1], Bos β-casein X-4P (f1-25) [2], Bos $\alpha_{s2}$-casein X-4P (f46-70) [3] and Bos $\alpha_{s2}$-casein X-4P (f1-21) [4] as follows:

[1]  $Gln^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-Lys$^{79}$  $\alpha_{s1}$(59-79)

[2]  $Arg^{1}$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-Arg$^{25}$ β(1-25)

[3]  Asn-Ala-Asn-Glu-Glu-Glu-Tyr-Ser-Ile-Gly-Ser(P)-Ser(P)-Ser(P)-Glu-Glu-Ser(P)-Ala-Glu-Val-Ala-Thr-Glu-Glu-Val-Lys$^{70}$ αs2(46-70)

[4]  $Lys^{1}$-Asn-Thr-Met-Glu-His-Val-Ser(P)-Ser(P)-Ser(P)-Glu-Glu-Ser-Ile-Ile-Ser(P)-Gln-Glu-Thr-Tyr-Lys$^{21}$  αs2 (1-21).

Other casein phosphopeptides that have activity in assisting in the stabilization of superloaded amorphous calcium phosphate complexes are those peptides containing the sequences Ser(P)-Xaa-Glu/Ser(P) where Ser(P) represents a phosphoseryl residue.

Therefore the phosphopeptides/phosphoproteins active in stabilizing superloaded amorphous calcium phosphate and amorphous calcium fluoride phosphate complexes are those containing the sequence -A-B-C-, where A is a phosphamino acid, preferably phosphoserine; B is any amino acid including a phosphoamino acid and C is one of the glutamate, aspartate or a phosphoamino acid.

Amorphous calcium phosphate stabilized by casein phosphopeptides as described in WO 98/40406 is available commercially in a product sold as Recaldent™ as provided by Recaldent Pty Ltd, Victoria, Australia. However, it would be desirable for an even more effective form of amorphous calcium phosphate stabilized by casein phosphopeptides to be available for treatments. Further, when Recaldent is dissolved in a carrier such as distilled water, there is inevitable leakage of ions into the surrounding water to form an equilibrium. This will, in some uses, reduce the calcium phosphate deliverable by the composition, such as for a treatment.

SUMMARY OF THE INVENTION

In one aspect, the present invention provides a "superloaded" phosphopeptide or phosphoprotein (PP) stabilized-amorphous calcium phosphate (ACP) or amorphous calcium fluoride phosphate (ACFP) complex. The complex may be formed at any pH (eg 3-10). Preferably the phosphopeptide includes the sequence -A-B-C-, where A is a phosphoamino acid, preferably phosphoserine, B is any amino acid including a phosphoamino acid and C is glutamic acid, aspartic acid or a phosphoamino acid. The phosphoamino acid may be phosphoserine. The PP is superloaded with calcium and phosphate ions. The calcium ions may be in the range 30-1000 mol Ca per mole of PP, or in the range of 30-100 or 30-50 mole Ca per mole of PP. In another embodiment, the mol Ca per mol of PP is at least 25, 30, 35, 40, 45 or 50. The phosphate ions will typically be present in a ratio to the calcium ions (Ca:P) of 1.5-1.8:1. In one embodiment, the ratio is about 1.58:1.

In a further aspect the present invention provides a phosphopeptide or phosphoprotein (PP) stabilized amorphous calcium phosphate or amorphous calcium fluoride phosphate complex having a calcium ion content greater than about 30 moles of calcium per mole of PP.

In a preferred embodiment, the calcium ion content is in the range of about 30 to 100 moles of calcium per mole of PP. More preferably, the calcium ion content is in the range of about 30 to about 50 moles of calcium per mole of PP.

The present invention further relates to an aqueous formulation of the PP stabilized ACP or ACFP complex described above.

It will also be understood that the term "comprises" (or its grammatical variants) as used in this specification is equivalent to the term "includes" and may be used interchangeably and should not be taken as excluding the presence of other elements or features.

Surprisingly, the activity of casein phosphopeptide-amorphous calcium phosphate (CPP-ACP) as produced using the method described in WO 98/40406, in remineralizing (repairing) enamel subsurface lesions (early stages of tooth decay) can be substantially increased by superloading the casein phosphopeptides with calcium and phosphate ions beyond the amount expected to be possible. The calcium can be in the form of $CaHPO_4$ or calcium lactate and sodium hydrogen phosphate or any other suitable form of calcium salt or phosphate salt.

The PP of the complexes of the present invention may be a casein phosphopeptide (CPP) which may be intact casein or a fragment of casein. The CPP-amorphous calcium phosphate complex formed may be a colloidal complex, where the core particles aggregate to form large (eg 100 nm) colloidal particles suspended in water.

The PP may be from any source; it may be present in the context of a larger polypeptide, including a full length casein polypeptide, or it may be isolated by tryptic or chemical (eg alkaline hydrolysis) digestion of casein or other phosphoamino acid rich proteins such as phosvitin, or by chemical or recombinant synthesis, provided that it comprises the sequence -A-B-C-. The sequence flanking this core sequence may be any sequence. However, those flanking sequences in $\alpha_{s1}(59-79)$ [1], $\beta(1-25)$ [2], $\alpha_{s2}(46-70)$ [3] and $\alpha_{s2}(1-21)$ [4] are preferred. The flanking sequences may optionally be modified by deletion, addition or conservative substitution of one or more residues. The amino acid composition and sequence of the flanking region are not critical although the preferred flanking regions appear to contribute to the structural action of the motif to maintain the conformation of the peptide so that all phosphoryl and carboxyl groups may interact with calcium ions.

In a preferred embodiment, the PP is selected from the group consisting of $\alpha_{s1}(59-79)$ [1], $\beta(1-25)$ [2], $\alpha_{s2}(46-70)$ [3] and $\alpha_{s2}(1-21)$ [4].

In a preferred embodiment, at least 40% by weight of the PP in the PP-stabilised ACP or ACFP is a mixture of proteins or protein fragments which are or contain one or more of the peptides [1] to [4] above. Preferably, at least 60%, more preferably at least 70%, by weight of the PP in the PP-stabilised ACP or ACFP is a mixture of proteins or protein fragments which are or contain the peptides [1] to [4].

The phosphopeptide is believed to stabilize the superloaded calcium, phosphate (and fluoride) to produce a metastable solution. This binding is believed to inhibit the growth of ACP or ACFP to a size that initiates nucleation and precipitation of calcium phosphate. In this way, calcium and other ions such as fluoride ions can be localised, for instance at a surface on a tooth to prevent demineralization and prevent or reduce formation of dental caries.

Thus, in a further aspect, the invention provides a stable, superloaded ACFP complex or a stable, superloaded ACP complex as described above, which complex acts as a delivery vehicle that co-localises ions including, but not limited to calcium, fluoride and phosphate ions at a target site. In a preferred embodiment, the complex is in a slow-release amorphous form that produces superior anti-caries efficacy. The target site is preferably teeth or bone.

In a further aspect, the invention also provides a method of producing a stable, superloaded complex of ACP or ACFP as described above, comprising the steps of:
(i) obtaining solutions comprising calcium, inorganic phosphate and fluoride (optional); and
(ii) admixing (i) with a solution comprising PP-ACP.

In a preferred embodiment, the PP is casein phosphopeptide (CPP).

In a further aspect of the present invention there is provided a method for increasing the calcium (and phosphate) ion content as ACP/ACFP of a PP stabilized-ACP and/or ACFP including the steps of
(i) obtaining solutions comprising calcium, inorganic phosphate and fluoride (optional); and
(ii) admixing (i) with a solution comprising PP-ACP and/or PP-ACFP. or
(i) obtaining powders containing calcium eg $CaHPO_4$, calcium lactate, etc. and
(ii) admixing (i) with a PP-ACP and/or PP-ACFP powder.

It has been found that increasing the calcium phosphate loading of PP-ACP complexes in the commercial product known as Recaldent™ may result in a higher viscosity preparation than is suitable for a particular application. Accordingly, it is useful for some applications to prepare the superloaded complexes by dry blending the PP-ACP with calcium phosphate (particularly $CaHPO_4$) for subsequent incorporation into a formulation, for example an oral care formulation such as a toothpaste or chewing gum.

In a further aspect of the present invention there is provided a method for producing a phosphopeptide or phosphoprotein (PP) stabilized amorphous calcium phosphate (ACP) and/or amorphous calcium fluoride phosphate (ACFP) complex having a calcium ion content above about 30 moles of calcium per mole of PP including the steps of:
(i) obtaining a solution including a PP-ACP and/or PP-ACFP complex; and
(ii) mixing with calcium and phosphate ions, while maintaining the solution at a pH of less than 7.

In a further aspect of the present invention there is provided a formulation of a PP stabilized ACP and/or ACFP complex together with at least an equal amount by weight of calcium phosphate. Preferably the calcium phosphate is $CaHPO_4$. Preferably, the calcium phosphate (e.g. $CaHPO_4$) is dry blended with the PP stabilized ACP and/or ACFP complex. In a preferred embodiment, the PP-ACP and/or PP-ACFP complex:calcium phosphate ratio is about 1:1-50. more preferably about 1:1-25, more preferably about 1:5-15. In one embodiment, the PP-ACP and/or PP-ACFP complex:calcium phosphate ratio is about 1:10.

In a further aspect of the present invention there is provided an oral care composition including a formulation of a PP stabilized ACP and/or ACFP complex together with at least an equal amount by weight of calcium phosphate as described above.

In a further aspect of the present invention there is provided a method for producing an oral care formulation that includes a phosphopeptide or phosphoprotein (PP) stabilized amorphous calcium phosphate (ACP) and/or amorphous calcium fluoride phosphate (ACFP) complex having a calcium ion content greater than about 30 moles of calcium per mole of PP when used in the oral cavity including the steps of:
(i) obtaining a powder including a PP-ACP and/or PP-ACFP complex;
(ii) dry blending with an effective amount of calcium phosphate; and
(iii) formulating the dry blended PP-ACP and/or PP-ACFP and calcium phosphate mixture into an oral care formulation.

Preferably, the form of calcium phosphate for dry blending is $CaHPO_4$.

Preferably the oral care formulation is selected from the group consisting of a toothpaste, a tooth crème; a chewing gum; lozenge; a mouthwash and a tooth powder. Without being bound by any theory or mode of action, it is believed that the "superloaded" phosphopeptide is able to deliver a sufficiently high concentration of calcium and phosphate ions, especially ACP and ACFP as the case may be, despite the inherent dilution resulting from the incorporation of the complexes into a physiologically acceptable carrier, and further dilution in, for example, saliva in dental applications. It thus maintains the ionic speciation of the calcium and phosphate ions. The invention is directed to greater amounts of ACP-ACFP at the site of delivery. This can be achieved by a starting material of higher ACP/ACFP content and/or reduced loss or leakage of ACP/ACFP between manufacture and use.

These superloaded complexes are also useful as dietary supplements in subjects who for any reason, such as dietary intolerance, allergy, or religious or cultural factors, are unable or unwilling to consume dairy products in an amount sufficient to supply their dietary calcium requirements. The superloaded complexes of the invention are useful as calcium supplements in subjects in need of stimulation of bone growth, for example subjects undergoing fracture repair, joint replacement, bone grafts, or craniofacial surgery.

In a further aspect of the present invention there is provided a method for remineralizing teeth comprising applying to the teeth a superloaded complex as described above, desirably in a pharmaceutically acceptable carrier. The complex may contain calcium phosphate, calcium fluoride or both. The method is preferably applied to a subject in need of treatment.

In a further aspect, the present invention provides a method for remineralizing a dental surface or subsurface including applying to the dental surface or subsurface a phosphopeptide or phosphoprotein (PP) stabilized amorphous calcium phosphate and/or amorphous calcium fluoride phosphate complex having a calcium ion content greater than about 30 moles of calcium per mole of PP.

In a further aspect of the present invention there is provided the use of a phosphopeptide or phosphoprotein (PP) stabilized amorphous calcium phosphate and/or amorphous calcium fluoride phosphate complex having a calcium ion content greater than about 30 moles of calcium per mole of PP in the manufacture of a medicament for remineralizing a dental surface or subsurface.

In a further aspect of the present invention there is provided the use of a phosphopeptide or phosphoprotein (PP) stabilized amorphous calcium phosphate and/or amorphous calcium fluoride phosphate complex having a calcium ion content greater than about 30 moles of calcium per mole of PP for remineralizing a dental surface or subsurface.

Preferably the dental surface or subsurface is dental enamel, more preferably a surface or subsurface lesion in the dental enamel.

The stable ACFP or ACP superloaded complex may be incorporated into or form in oral care compoistions such as toothpaste, mouth washes or formulations for the mouth. This may, for example, aid in the prevention and/or treatment of dental caries or tooth decay. The ACFP or ACP superloaded complex (which may comprise solely CPP-ACP and/or -ACFP complexes, or CPP-ACP and/or -ACFP complexes with calcium phosphate, e.g. $CaHPO_4$) may comprise 0.01-50% by weight of the composition, preferably 0.1%-25%, more preferably 0.5%-20% and optionally 0.5%-10%. For oral compositions, it is preferred that the amount of the CPP-ACP and/or CPP-ACFP administered is 0.01-50% by weight, preferably 0.5%-20% or 0.5%-10% by weight of the composition. In a particularly preferred embodiment, the oral composition of the present invention contains about 1-5% superloaded CPP-ACP (sCPP-ACP). The oral composition of this invention which contains the above-mentioned agents may be prepared and used in various forms applicable to the mouth such as dentifrice including toothpastes, toothpowders and liquid dentifrices, mouthwashes, troches, chewing gums, dental pastes, gingival massage creams, gargle tablets, dairy products and other foodstuffs. The oral composition according to this invention may further include additional well known ingredients depending on the type and form of a particular oral composition.

In certain preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 3 to about 10 and typically from about 5.0 to 7.0. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

In one embodiment, the oral composition according to the present invention has a pH of about 5.5.

Accordingly, in a further aspect of the present invention there is provided a composition for remineralizing a dental surface or subsurface including a phosphopeptide or phosphoprotein (PP) stabilized amorphous calcium phosphate and/or amorphous calcium fluoride phosphate complex having a calcium ion content greater than about 30 moles of calcium per mole of PP together with a pharmaceutically acceptable carrier and/or excipient.

In a further aspect of the present invention there is provided a composition for remineralizing a dental surface or subsurface consisting essentially of a phosphopeptide or phosphoprotein (PP) stabilized amorphous calcium phosphate and/or amorphous calcium fluoride phosphate complex having a calcium ion content greater than about 30 moles of calcium per mole of PP together with a pharmaceutically acceptable carrier and/or excipient.

In another embodiment, the oral composition according to the present invention contains a calcium chelator, eg. pyrophosphate, polyphosphate, citrate, EDTA, etc.

In other desirable forms of this invention, the oral composition may be substantially solid or pasty in character, such as toothpowder, a dental tablet or a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminum silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 $cm^2$/g., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal aluminosilicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner, for example as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in an amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, a jar of mouthrinse will have a label describing it, in substance, as a mouthrinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, nonionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g: sorbitan monostearate) and polypropyleneoxide (e.g. Pluronic materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

The invention also provides use of a composition as described above. In the preferred practice of this invention an oral composition according to this invention such as mouthwash or dentifrice containing the composition of the present invention is preferably applied regularly to the gums and teeth, such as every day or every second or third day or preferably from 1 to 3 times daily, at a pH, preferably of about 3.0 to about 10.0 or more preferably 5.0 to about 9.0, for at least 2 weeks up to 8 weeks or more up to a lifetime. In one embodiment, the pH of the oral composition is about 5.0, 5.5, 6.0, 6.5, 7.0, 7.5, 8.0, 8.5, 9.0.

The compositions of this invention can also be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like.

In another embodiment, the complex of the invention is formulated to form a dietary supplement preferably comprising 0.1-100% w/w, more preferably 1-50% w/w, most preferably 1-10% and particularly 2% w/w of a comestible. The complex may also be incorporated into food products.

In a further aspect, the invention provides compositions including pharmaceutical compositions comprising any of the superloaded ACFP and/or ACP complexes as described above together with a pharmaceutically-acceptable carrier. Such compositions may be selected from the group consisting of dental, anticariogenic compositions, therapeutic compositions and dietary supplements. Dental compositions or therapeutic compositions may be in the form of a gel, liquid, solid, powder, cream or lozenge. Therapeutic compositions may also be in the form of tablets or capsules. In one embodiment, the superloaded ACP and/or ACFP complexes are substantially the only remineralizing active components of such a composition. In a further embodiment the superloaded ACP and/or ACFP complexes form after the composition, as an oral care composition, is contacted with saliva in the oral cavity.

In a further aspect, there is provided a method of treating or preventing dental caries or tooth decay, dental erosion/corrosion, dentinal hypersensitivity and dental calculus comprising the step of administering a complex or composition of the invention to the teeth or gums of a subject in need of such treatments. Topical administration of the complex is preferred.

According to a further aspect of the invention there is provided a composition for dental restoration, including a dental restorative material to which has been added a superloaded ACFP and/or ACP complex according to the present invention. The base of the dental restorative material can be a glass ionomer cement, a composite material or any other restorative material which is compatible. It is preferred that the amount of superloaded CPP-ACP complex or superloaded CPP-ACFP complex included in the dental restorative material is 0.01-80% by weight, preferably 0.5-10% and more preferably 1-5% by weight. The dental restorative material of this invention which contains the above mentioned agents may be prepared and used in various forms applicable to dental practice. The dental restorative material according to this invention may further include other ions, eg. antibacterial ions $Zn^{2+}$, $Ag^+$, etc or other additional ingredients depending on the type and form of a particular dental restorative material. It is preferable that the pH of the superloaded CPP-ACP complex or superloaded CPP-ACFP complex be between 2-10, more preferably 5-9 and even more preferably 5-7. It is preferable that the pH of the dental restorative material containing the superloaded CPP-ACP complex or superloaded ACFP complex be between 2-10, more preferably 5-9 and even more preferably 5-7.

The invention is also directed to a method of manufacture of a restorative composition. Preferably, the method includes the addition of a superloaded ACP and/or ACFP complex as described above, to a base dental restorative material. The invention also relates to use of a restorative composition as stated above for the treatment and/or prevention of dental caries.

In a further aspect of the present invention there is provided a kit for use in the preparation of a composition for dental restoration including (a) dental restorative material and (b) a phosphopeptide or phosphoprotein (PP) stabilized amorphous calcium phosphate and/or amorphous calcium fluoride phosphate complex having a calcium ion content greater than about 30 moles of calcium per mole of PP. The kit may optionally include instructions for use for the preparation of a composition for dental restoration.

In a preferred embodiment, the dental restorative material is a porous dental cement. In a further preferred embodiment, the dental restorative material is a glass ionomer cement. Without being bound by any theory or mode of action, it is believed that micropores in certain types of porous dental cement, such as glass ionomer cements, allow the passage of the complexes of the present invention to the dental surface to promote remineralization of the dental material.

The invention also relates to a kit for use in the preparation of a composition for dental restoration including (a) dental restorative material and (b) superloaded CPP-ACP complex and/or superloaded CPP-ACFP complex. The kit may optionally include instructions for use for the preparation of a composition for dental restoration.

The invention also relates to a kit for use in the preparation of a composition for dental restoration including (a) dental restorative material (b) casein phosphopeptide (c) calcium ions and (d) phosphate ions, and optionally fluoride ions. The kit may optionally include instructions for use for the preparation of a composition for dental restoration.

The invention also provides a method of treatment and/or prevention of dental caries, dental erosion/corrosion, dental hypersensitivity and dental calculus in animals including humans including providing the composition according to the invention, or manufactured according to the invention, and applying to teeth in an animal in need of treatment and/or prevention.

In a further aspect, the invention relates to methods of treating one or more conditions related to calcium loss from the body, especially from the bones, calcium deficiency, calcium malabsorption, or the like. Examples of such conditions include, but are not limited to, osteoporosis and osteomalacia. In general any condition which can be improved by increased calcium bioavailability is contemplated. in a further aspect of the present invention there is provided the use of a phosphopeptide or phosphoprotein (PP) stabilized amorphous calcium phosphate and/or amorphous calcium fluoride phosphate complex having a calcium ion content greater than about 30 moles of calcium per mole of PP in the manufacture of a composition for the treatment and/or prevention of dental caries, dental erosion/corrosion, dental hypersensitivity, and/or dental calculus.

In a further aspect of the present invention there is provided the use of a composition including a phosphopeptide or phosphoprotein (PP) stabilized amorphous calcium phosphate and/or amorphous calcium fluoride phosphate complex having a calcium ion content greater than about 30 moles of calcium per mole of PP for the treatment and/or prevention of dental caries, dental erosion/corrosion, dental hypersensitivity, or dental calculus.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

The invention will now be described with reference to the following non-limiting examples.

EXAMPLE 1

Recaldent™ (CPP-ACP) was purchased from Recaldent Pty Ltd, Victoria, Australia. The product (#841117) contained 14.3% calcium, 22.3% phosphate and 47% casein phosphopeptide on a weight basis. The product was dissolved at 0.5% and adjusted to pH 5.5 by the addition of HCl. Calcium and phosphate ions were then added by titrating 3.25 M $CaCl_2$ and 2M $NaH_2PO_4$ while keeping the pH at 5.5 with the addition of 2.5 M NaOH. The titration of calcium and phosphate ions was continued until the solution became translucent. The concentration of calcium and phosphate added was recorded.

The solution may also be formed by titrating calcium and phosphate ions into a 0.5% CPP-ACP solution and letting the pH fall to 5.5 by the addition of further calcium phosphate.

TABLE 1

Calcium and phosphate levels of normal and superloaded CPP-ACP

| | Calcium | | Phosphate | |
|---|---|---|---|---|
| | mmol/L | mol/mol CPP | mmol/L | mol/mol CPP |
| Normal 0.5% w/v CPP-ACP | 17.8 | 22.8 | 11.6 | 14.8 |
| Superloaded 0.5 w/v CPP-ACP (sCPP-ACP) | 37.8 | 48.3 | 23.6 | 30.2 |

These results demonstrate that CPP-ACP can be superloaded with calcium and phosphate ions to produce thermodynamically stable complexes in a metastable solution.

EXAMPLE 2

In another example Recaldent™ (CPP-ACP) powder was dry blended with $CaHPO_4$ powder in the ratio CPP-ACP: $CaHPO_4$ equals 1:10 on a weight basis. This powder was then added to sugar-free gum and toothpaste formulations at 1-5% w/w.

EXAMPLE 3

Comparison of Remineralization of Enamel Subsurface Lesions In vitro by Normal CPP-ACP and Superloaded CPP-ACP (sCPP-ACP The polished enamel surface of extracted human third molars were sawn as a slab (8×4 $mm^2$) and covered with acid resistant nail varnish to form an occlusal-half and a gingival-half mesiodistal window (1×7 $mm^2$) separated by 1 mm [Reynolds E. C. (1997) *J. Dent. Res.* 76, 1587-1595]. Subsurface enamel lesions were created in these windows using the Carbopol method of White [White D. J. (1987) Caries Res 21, 228-242] as modified by Reynolds [Reynolds E. C. (1997) *J. Dent. Res.* 76, 1587-1595]. The enamel slabs were sawn in half to 4×4 $mm^2$ blocks. The gingival-half lesion on one block and the occlusal-half lesion on the other block were sealed with varnish to create the demineralized controls as described by Reynolds [Reynolds E. C. (1997) *J. Dent. Res.* 76, 1587-1595].

The enamel half-lesions were exposed to the two different remineralization solutions for 10 days at 37° C. without mixing. The remineralization solutions were 0.5% w/v CPP-ACP adjusted to pH 5.5 with HCl and superloaded CPP-ACP prepared in Example 1.

After remineralization each pair of blocks was dehydrated in ethanol and embedded in methyl-methacrylate resin (Paladur, Kulzer, Germany). Three 200-300 μm sections were cut perpendicular to the lesion surface, lapped down to 80±5 m and radiographed beside an aluminium stepwedge of 10×14 μm thick increments as described previously.

Radiographic images of the lesions were viewed via transmitted light through a Dilux 22 microscope (Ernst Leitz Wetzlar, Germany). The images were acquired by video camera (Sony DXC 930P) and digitized (Scion imaging corporation, colour grabber 7) under the control of imaging software (Optimas 6.2). Images of the lesions, controls and the aluminium stepwedge were scanned as previously described by Shen et al. [Shen P. et al., (2001) *J. Dent. Res.* 80, 2066-2070]. The enamel section thickness was measured and volume percentage mineral data determined using the equation of Angmar [Angmar B. et al., (1963) *Ultrastructural Res* 8, 12-23] as previously described by Shen et al. [Shen P. et al., (2001) *J.*

Dent. Res. 80, 2066-2070]. The percentage remineralization (% R) was also calculated as previously described by Shen et al. [Shen P. et al., (2001) *J. Dent Res.* 80, 2066-2070].

Figure 1:
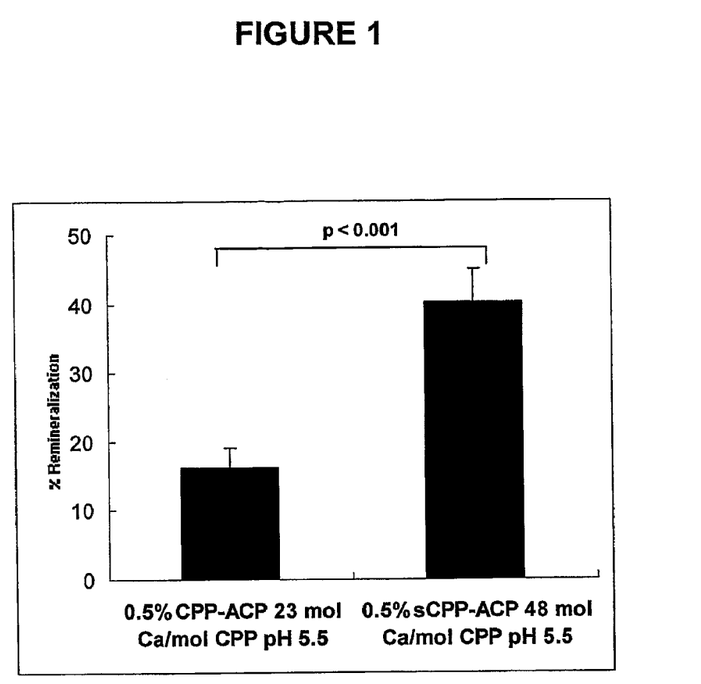
FIG. 1: Enhanced remineralization of enamel subsurface lesions in vitro by CPP superloaded with calcium and phosphate ions.

The remineralization of the enamel subsurface lesions is shown in FIG. 1.

The results of FIG. 1 demonstrate that a superloaded CPP-ACP (sCPP-ACP) solution is superior to a normal CPP-ACP solution in remineralization of enamel subsurface lesions in vitro.

EXAMPLE 4

Figure 2:
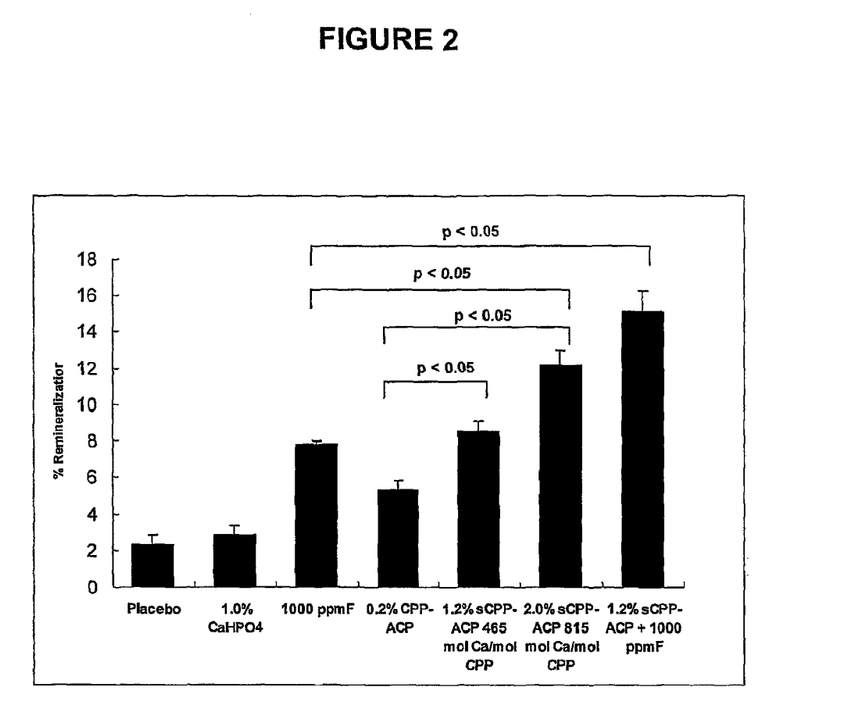
FIG. 2. Enhanced remineralization of enamel subsurface lesions in situ by toothpaste containing CPP superloaded with calcium phosphate.

The ability of toothpaste formulations containing superloaded CPP-ACP (sCPP-ACP) to remineralize enamel subsurface lesions was investigated in a randomized, cross-over, double-blind in situ clinical study using the protocol of Reynolds et al. [Reynolds E. C. et al., (2003) *J Dent Res.* 82, 206-211]. Ten subjects wore removable palatal appliances with six, human enamel, half-slabs containing sub-surface demineralized lesions prepared as described in Example 3. The other half of each enamel slab was stored in a humidified container and was used as the control demineralized lesion. There were seven treatments in the study, toothpaste B containing 0.2% w/w normal CPP-ACP, toothpaste C containing 0.2% CPP-ACP/1.0% CaHPO$_4$ (referred to in FIG. 2 and Example 5 as "1.2% sCPP-ACP"), toothpaste E containing 1.0% CaHPO$_4$, toothpaste F containing 1000 ppm F, toothpaste G containing 1.2% sCPP-ACP plus 1000 ppmF, toothpaste D containing 0.2% CPP-ACP/1.8% CaHPO$_4$ (referred to in FIG. 2 and Example 5 as "2.0% sCPP-ACP"), and a control toothpaste A (placebo). The pastes were used for 30 s periods, four times per day. The appliances were worn while using the paste and then for 1 hr after using the paste. Each treatment was for 14 days duration and each of the ten subjects carried out each treatment with a one week rest between the treatments. At the completion of each treatment the enamel slabs were removed, paired with their respective demineralized control, embedded, sectioned and subjected to microradiography and computer-assisted densitometric image analysis to determine the level of remineralization. The results presented as percentage enamel remineralization (% R) are shown in FIG. 2 and demonstrate that 0.2% CPP-ACP superloaded with either 1.0% CaHPO$_4$ (1.2% sCPP-ACP) or 1.8% CaHPO$_4$ (2.0% sCPP-ACP) remineralizes enamel subsurface lesions significantly better than the normal 0.2% CPP-ACP or the CaHPO$_4$ alone at the same concentration. The 2.0% sCPP-ACP paste was significantly better than the paste containing 1000 ppm fluoride. Further, 1.2% sCPP-ACP plus 1000 ppm F showed an additive effect over 1.2% sCPP-ACP or 1000 ppm F alone.

EXAMPLE 5

Toothpaste Formulations Containing Superloaded CPP-ACP (sCPP-ACP)

Formulation 1

| Ingredient | % w/v | | |
|---|---|---|---|
| | 1 | 2 | 3 |
| Sorbitol | 53.0 | 53.0 | 53.0 |
| Silica (Zeodent 119) | 20.0 | 20.0 | 20.0 |
| Purified water | balance | balance | balance |
| Sodium lauryl sulphate | 4.0 | 4.0 | 4.0 |
| sCPP-ACP | 1.2 | 1.2 | 2.0 |
| Sodium monofluorophosphate | 0.3 | — | — |
| Flavour | 1.0 | 1.0 | 1.0 |
| Sodium carboxymethyl cellulose | 0.75 | 0.75 | 0.75 |
| Titanium dioxide | 0.525 | 0.525 | 0.525 |
| Xanthan gum | 0.475 | 0.475 | 0.475 |
| Sodium saccharin | 0.350 | 0.350 | 0.350 | pH adjusted to 7.0 with phosphoric acid

Formulation 2

| Ingredient | % w/v | % w/v | % w/v |
|---|---|---|---|
| Sorbitol | 22.0 | 22.0 | 22.0 |
| Irish Moss | 1.0 | 1.0 | 1.0 |
| Gantrez | 19.0 | 19.0 | 19.0 |
| Purified water | balance | balance | balance |
| Sodium monofluorophosphate | — | — | 0.76 |
| Sodium saccharine | 0.3 | 0.3 | 0.3 |
| Pyrophosphate | 2.0 | 2.0 | 2.0 |
| Hydrated alumina | 47.0 | 47.0 | 47.0 |
| Flavour | 0.95 | 0.95 | 0.95 |
| sCPP-ACP | 1.0 | 2.0 | 2.0 |
| Sodium lauryl sulphate | 2.0 | 2.0 | 2.0 | pH adjusted to 5-7 with NaOH

Formulation 3

| Ingredient | % w/v |
|---|---|
| Dicalcium phosphate dihydrate | 45.0 |
| Sorbitol | 10.0 |
| Glycerol | 10.0 |
| Sodium carboxymethyl cellulose | 1.0 |
| Sodium lauryl sulphate | 1.5 |
| Sodium lauryl sarconisate | 0.5 |
| Flavour | 1.0 |
| Sodium saccharine | 0.1 |
| Sodium monofluorophosphate | 0.3 |
| Chlorhexidine gluconate | 0.01 |
| Dextranase | 0.01 |
| sCPP-ACP | 5.0 |
| Purified water | balance | pH adjusted to 5-7 with phosphoric acid

Formulation 4

| Ingredient | % w/v |
|---|---|
| Sorbitol | 22.0 |
| Irish moss | 1.0 |
| Gantrez | 19.0 |
| Purified water | balance |
| Sodium saccharin | 0.3 |
| Pyrophosphate | 2.0 |
| Hydrated alumina | 43.0 |
| Sodium monofluorophosphate | 0.3 |
| Flavour | 0.95 |
| sCPP-ACP | 5.0 |
| Sodium lauryl sulphate | 2.0 | pH adjusted to 5.5 with NaOH

Formulation 5

| Ingredient | % w/v |
|---|---|
| Dicalcium phosphate dihydrate | 45.0 |
| Sorbitol | 10.0 |
| Glycerol | 10.0 |
| Sodium carboxymethyl cellulose | 1.0 |
| Sodium lauryl sulphate | 1.5 |
| Sodium lauryl sarconisate | 0.5 |
| Flavour | 1.0 |
| Sodium saccharine | 0.1 |
| Chlorhexidine gluconate | 0.01 |
| Dextranase | 0.01 |
| Sodium monofluorophosphate | 0.3 |
| sCPP-ACP | 5.0 |
| Purified water | balance | pH adjusted to 5.5 with phosphoric acid

Formulation 6

| Ingredient | % w/v 1 | % w/v 2 |
|---|---|---|
| Sorbitol | 53.0 | 53.0 |
| Silica (Zeodent 119) | 20.0 | 20.0 |
| Purified water | balance | balance |
| Sodium lauryl sulphate | 4.0 | 4.0 |
| sCPP-ACP | 5.0 | 5.0 |
| Sodium monofluorophosphate | — | 0.3 |
| Sodium dihydrogen phosphate | 1.45 | 1.45 |
| Flavour | 1.0 | 1.0 |
| Sodium carboxymethyl cellulose | 0.75 | 0.75 |
| Titanium dioxide (Rutile) | 0.525 | 0.525 |
| Xanthan gum | 0.475 | 0.475 |
| Sodium saccharin | 0.350 | 0.350 |
| Sodium fluoride | 0.243 | — | pH adjusted to 5-7 with phosphoric acid/NaOH

Formulation 7

| Ingredient | % w/v 1 | % w/v 2 |
|---|---|---|
| Sorbitol (70% solution) | 31.0 | 31.0 |
| Purified water | balance | balance |
| Silica | 17.0 | 17.0 |
| Glycerol | 8.0 | 8.0 |
| Sodium lauryl sulphate | 4.0 | 4.0 |
| Polyethylene glycol 300 | 1.0 | 1.0 |
| Sodium fluoride | 0.243 | — |
| Titanium dioxide (Rutile) | 0.525 | 0.525 |
| Xanthan gum | 0.475 | 0.475 |
| Sodium carboxymethyl cellulose | 0.5 | 0.5 |
| Sodium saccharine | 0.286 | 0.286 |
| Sodium acid pyrophosphate | 2.4 | 2.4 |
| Tetra sodium pyrophosphate | 2.2 | 2.2 |
| Flavour | 1.0 | 1.0 |
| sCPP-ACP | 5.0 | 5.0 |
| Sodium monofluorophosphate | — | 0.3 | pH adjusted to 5-7 with phosphoric acid/NaOH

EXAMPLE 6

Mouthwash Formulations

Formulation 1

| Ingredient | % w/v |
|---|---|
| Ethanol | 10.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| sCPP-ACP | 5.0 |
| Water | balance | pH adjusted to 5.5 using phosphoric acid/NaOH

Formulation 2

| Ingredient | % w/v |
|---|---|
| Gantrez S-97 | 2.5 |
| Glycerine | 10.0 |
| Flavour oil | 0.4 |
| Chlorhexidine gluconate | 0.01 |
| Lauroyl diethanolamide | 0.2 |
| sCPP-ACP | 5.0 |
| Water | balance | pH adjusted to 5.5 using phosphoric acid/NaOH

EXAMPLE 7

Lozenge Formulation

| Ingredient | % w/v |
|---|---|
| Sugar/sugar alcohol | 75-80 |
| Corn syrup | 1-20 |
| Flavour oil | 1-2 |
| sCPP-ACP | 5.0 |
| Mg stearate | 1-5 |
| Water | balance | pH adjusted to 5.5 using phosphoric acid/NaOH

EXAMPLE 8

Chewing Gum Formulation

| Ingredient | % w/v |
|---|---|
| Gum base | 30 |
| Calcium carbonate | 2.0 |
| Crystalline sorbitol | 53.0 |
| Glycerine | 0.5 |
| Flavour oil | 0.1 |
| sCPP-ACP | 5.0 |
| Water | balance | pH adjusted to 5.5 using citric acid

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for producing an oral care formulation comprising: a phosphopeptide or phosphoprotein (PP) stabilized amorphous calcium phosphate (ACP) and/or amorphous calcium fluoride phosphate (ACFP) complex having a calcium ion content of 30 moles or greater of calcium per mole of PP, the method including the steps of:
   (i) providing the powder comprising a phosphopeptide or phosphoprotein (PP) stabilized amorphous calcium phosphate (ACP) and/or amorphous calcium fluoride phosphate (ACFP) complex;
   (ii) dry blending the said powder with an effective amount of calcium phosphate; and
   (iii) formulating the dry blended PP-ACP and/or PP-ACFP and calcium phosphate mixture into an oral care formulation.

2. An oral care formulation produced by the method of claim 1.

3. The method according to claim 1, wherein the formulation is selected from the group consisting of toothpastes, toothpowders, liquid dentifrices, gel dentifrices, mouthwashes, mouth rinses, troches, chewing gums, dental pastes, gingival massage creams, gargle tablets, dietary supplements, dental restoratives and varnishes.

4. The method according to claim 1, wherein the calcium phosphate is in the form of $CaHPO_4$.

5. The method according to claim 1, wherein the amount of calcium phosphate in step (ii) is at least equal by weight to the PP-ACP and/or PP-ACFP complex.

6. The method according to claim 1, wherein the PP comprises the sequence -A-B-C-,
   wherein A is a phosphoserine, B is any amino acid comprising a phosphoamino acid and C is any one of glutamate, aspartate or a phosphoserine.

7. The method according to claim 6, wherein A is a phosphoserine, B is any amino acid and C is a phosphoserine.

8. The method according to claim 1, wherein the calcium ion content of the complex is in the range of 30 to 50 moles of calcium per mole of PP.

9. The method according to claim 1, wherein the calcium ion content of the complex is in the range of 30 to 100 moles of calcium per mole of PP.

10. The method according to claim 3, wherein the formulation is a toothpaste.

11. The method according to claim 1, wherein the PP-ACP and/or PP-ACFP and calcium phosphate comprises 0.01% to 50% by weight of the formulation.

* * * * *